(12) United States Patent
Hall et al.

(10) Patent No.: US 7,939,480 B2
(45) Date of Patent: May 10, 2011

(54) CLEANING COMPOSITION

(75) Inventors: Christopher John Hall, Chester (GB); Najem Yaqub, Oldharr (GB)

(73) Assignee: PZ Cussons (International) Limited (GB)

( * ) Notice: Subject to any disclaimer, the term of this patent is extended or adjusted under 35 U.S.C. 154(b) by 465 days.

(21) Appl. No.: 11/803,849

(22) Filed: May 16, 2007
(Under 37 CFR 1.47)

(65) Prior Publication Data

US 2008/0261842 A1 Oct. 23, 2008

Related U.S. Application Data

(63) Continuation-in-part of application No. 11/247,977, filed on Oct. 11, 2005, now abandoned, which is a continuation of application No. 10/205,729, filed on Jul. 26, 2002, now abandoned, which is a continuation-in-part of application No. 09/810,772, filed on Dec. 6, 2000, now abandoned, which is a continuation of application No. 08/983,493, filed as application No. PCT/GB96/01744 on Jul. 19, 1996, now abandoned.

(30) Foreign Application Priority Data

Jul. 21, 1995 (GB) .................................. 9515023.1

(51) Int. Cl.
*C11D 1/94* (2006.01)
*C11D 17/00* (2006.01)
*A61K 8/02* (2006.01)

(52) U.S. Cl. ........ 510/140; 510/120; 510/158; 510/403; 510/406; 424/401

(58) Field of Classification Search .................. 510/120, 510/140, 158, 403, 406; 424/401; 514/846
See application file for complete search history.

(56) References Cited

U.S. PATENT DOCUMENTS

| | | | | |
|---|---|---|---|---|
| 5,078,991 | A | * | 1/1992 | Birtwistle et al. ............. 510/122 |
| 5,248,495 | A | * | 9/1993 | Patterson et al. ............... 424/73 |
| 5,306,444 | A | * | 4/1994 | Kitamura et al. ............. 510/490 |
| 5,560,918 | A | * | 10/1996 | Wivell et al. .................. 424/401 |
| 5,599,549 | A | * | 2/1997 | Wivell et al. .................. 424/401 |
| 6,001,344 | A | * | 12/1999 | Villa et al. ................. 424/78.02 |
| 2004/0258643 | A1 | * | 12/2004 | Yaqub et al. ................. 424/70.2 |

FOREIGN PATENT DOCUMENTS

WO WO 95/13349 A1 * 5/1995

* cited by examiner

*Primary Examiner* — Lorna M Douyon
(74) *Attorney, Agent, or Firm* — Salter & Michaelson

(57) ABSTRACT

A post-foaming personal cleaning composition in the form of a gel for use in an aerosol container. This composition includes a base material of a surfactant in an amount not less than 7 % by weight and a thickener that is a blend of at least one of glyceryl ester, and a glyceryl ester derivative with at least one of a betaine and a gum. The base material preferably has a viscosity greater than 9,500 cps. The composition also includes a foam forming material, above 9 % by weight of the composition with at least a part of the foam forming material being maintained in suspension in the composition until after the composition is dispensed from the aerosol container. The foam forming material is preferably a saturated aliphatic hydrocarbon having from 4 to 5 carbons and the composition is in the form of a gel prior to inclusion of the foam forming material.

13 Claims, 1 Drawing Sheet

CLEANING COMPOSITION

RELATED APPLICATIONS

This application is a continuation-in-part of U.S. Ser. No. 11/247,977 filed on Oct. 11, 2005, now abandoned, which is a continuation of Ser. No. 10/205,729 filed on Jul. 26, 2002, now abandoned, which is a continuation-in-part of Ser. No. 09/810,772 filed on Dec. 6, 2000, now abandoned, which is a continuation of Ser. No. 08/983,493 filed on Jun. 15, 1998, now abandoned.

This application derives from international application PCT/GB 96/01744 filed on Jul. 19, 1996, and claims priority from GB 9515023.1 filed on Jul. 21, 1995.

TECHNICAL FIELD

This invention relates to a cleaning composition and more particularly a personal cleaning, composition intended for use in a shower.

BACKGROUND OF THE INVENTION

Although personal cleaning compositions have been developed for showers, such as shower gels, a significantly large number of people prefer to use a conventional bar of soap rather than a shower gel. It is believed that one factor responsible for resistance to the use of shower gels is connected to lather generation. Shower gels are provided in containers or dispensers from which the user must obtain a dose. This finite amount of gel will produce a finite amount of lather. In order to produce the lather the user must apply shear to the gel, for example by rubbing the gel on a part of the body. However, the lather so produced is soon washed away by the stream of water from the shower head. Indeed, in some cases the gel can be washed away and wasted before the user has been able to apply the gel to a part of the body and create a lather. A bar of soap, on the other hand, provides a continuous supply of lather even if the stream of water from the shower head is directed onto the soap bar.

In order to deal with this problem it has been proposed to make provision for the generation of lather from a shower gel as soon as possible after the gel is dispensed. One way of effecting this is to use an aerosol to contain the gel. On release of the contents of the aerosol a foam in the form of a mousse is formed substantially instantaneously. The problem with this proposal is that it is a widely held belief that the generation of a lather by the user of a cleaning composition is essential for satisfactory cleaning. The application of a pre-formed lather, even if perfectly efficacious is not thought to be so.

WO96/09032A discloses a soap free post-foaming gel composition which is particularly intended for wet shaving using a razor. The composition is preferably prepared by forming a base material consisting of water, a water soluble N-acyl sarcosinate salt and a non-volatile paraffinic hydrocarbon. To this thin, relatively low viscosity mixture is added a volatile hydrocarbon such as isopentane. This addition causes the formation of a gel structure. While this composition is satisfactory for its intended purpose of a shaving foam it does not perform well for personal washing mainly because it gives an uncomfortable "stripped" feeling to the skin. This effect is believed to be caused by the composition removing the natural skin lipids which gives a "squeaky" skin feel which users dislike.

The present invention is intended to provide a post foaming gel composition for personal cleaning which feels good to use.

The Invention

According to the invention there is provided a cleaning composition in the form of a gel for use in an aerosol container. The composition comprises (a) a base material which consists at least of a surfactant in an amount not less than 7.0% by weight of the total weight of the composition, and a thickener that is a blend of at least one of a glycerol ester, and a glycerol ester derivative with at least one of a betaine and a gum. The base material has a viscosity greater than 9,500 cps; and (b) a foam forming material, above 9% by weight of the composition, at least a part of the foam forming material being maintained in suspension in the composition until after the composition is dispensed from the aerosol container. The foam forming material is a saturated aliphatic hydrocarbon having from 4 to 5 carbons, and the composition is in the form of a gel prior to inclusion of the foam forming material.

An important feature of the invention is the viscosity of the base material which is such that the base material is already in the form of a gel prior to the inclusion of the propellant. The minimum viscosity of the base material is, as stated, 9,500 cps (measured on a Brookfield viscometer [model: Synchro-Lectric RNT viscometer; spindle 4/speed 20] at room temperature i.e 20° C.).

Preferably, however, the viscosity of the base material is considerably higher, for example above 20,000 cps and more preferably above 30,000 cps and particularly preferably above 60,000 cps (on the same basis of measurement). The base material in the form of a gel is stable and enables a high level of propellant to be included in the composition. The viscosity of the gel composition provides for control of the rate of foaming when the composition is dispensed from the container. In addition the relatively high viscosity of the composition gives stability to the composition during storage prior to use.

It has been found that the foam produced by compositions of the invention have a very different structure to the prior art foams produced from post-foaming compositions. The prior art foam consists of a plurality of small closed cells with a few slightly larger cells here and there. The foam obtained with the invention comprises a plurality of large cells, that is to say up to ten times the size of the largest cells in the prior art foam, with smaller cells filling in the spaces between the larger cells. These smaller cells are in most cases bigger than the largest cells in the prior art foam. The foam of the invention has a high volume and a creamy texture and does not impart the so-called stripping feel to the skin that is experienced with prior art foams.

A preferred embodiment of the invention is intended for use in a shower. In that embodiment a level of propellant is used, for example above 9.0% by weight, which is higher than in prior art foams used for shaving. It has been found that the composition of the invention with such higher levels of propellant are easily rinsed away when used in a shower or other circumstances such as hand washing. Prior art foam, especially foam intended for shaving, with its small cell structure is less readily rinsed away. A shower foam with such a "tight" structure is less readily rinsed away, but instead remains as a foam when washed from the skin and can clog up the waste outlet.

When the composition of the invention is used the formation of a foam or lather is delayed for a short time after the composition is dispensed by virtue of the propellant gas being retained in suspension. Very shortly after dispense agitation of the composition by the user causes the gas to permeate through the composition and a lather or foam is formed. Thus it appears that the user is responsible for creating the lather or foam as with conventional cleaning materials and the composition is seen as providing the behavior expected for a good cleaning operation.

The thickener used in the composition of the invention must be one that will maintain the propellant gas in suspension until after the composition is dispensed from the aerosol container. Thickeners useful in the present invention include polyacrylic acids, natural and synthetic clays, alginates, collagen thickeners, cellulose thickeners, gelatin, glycerin based thickeners, guar thickeners, polyquaternium thickeners, xantham gum, acrylate copolymers polyethylene glycol thickeners and glycol esters. The preferred thickeners include alkanolamides such as coconut diethanolamide, glyceryl esters and derivatives and blends thereof such as glyceryl laurate together with cocamidopropyl betaine and guar gums such as hydroxypropyl trimonium chloride. The amount of thickener used depends upon the particular thickener employed. For example in the case of coconut diethanolamide from 0.05 to 20.0%, preferably from about 2 to 4% and more preferably 3.0% by weight will generally be adequate. With the glyceryl laurate/cocamidopropyl betaine blend amounts of from 0.05 to 30% preferably from 5 to 10% by weight are preferably employed.

The composition of the invention requires sufficient foam forming material so that the composition does not thin and separate. In addition the detergent should also be present in an amount which does not result in the composition thinning. Preferably the amount of detergent should be in the range 0.05 to 60.0% and preferably not less than 7% and more preferably not less than 15% by weight of the total composition.

The particular foam forming material and surfactant system used in the composition is not critical and they can be chosen according to the particular type of composition that is being formulated.

The preferred foam forming materials are saturated aliphatic hydrocarbons having from 4 to 5 carbons such as n-butane, iso-butane, n-pentane and iso-pentane.

Detergents which can be used in this invention include anionic, cationic, nonionic, amphoteric surfactants and mixtures thereof. Detergents which are useful include alkyl polyglucosides, ethoxylated and non-ethoxylated metal alkyl sulfonates, sultaines, taurates, sarcosinates, sulfonates, ether carboxylates, glycinates, quaternary ammonium compounds, polysorbates, sugar esters, alky phosphates, propionates, amino acid surfactants, glycosides, alkanolamides and betaines.

The particularly preferred detergents used in the invention are anionic surfactants such as alkali metal alkyl ether sulphates, sulphosuccinates and acyl glutamates. A particularly preferred surfactant is sodium lauryl ether sulphate. If desired a mixture of surfactants can be used. These may be all anionic or may be a combination of anionic with one or more of nonionic, amphoteric and cationic surfactants.

The aerosol container may be any such container that can dispense a post foaming gel.

Water may be present in any desired amount.

Other Ingredients

Colorants that may be used in the present invention include compounds which cause a change in color or modify the visual appearance of the composition. Colorants may be selected from dyes, pigments, inks, paint, or chemicals. Suitable coloring agents may include red, black and yellow iron oxides, FD&C dyes, crystal violet, brilliant green, erichrome black T, methyl red, methyl orange, alizarin yellow, and Bengal pink, as well as merocyanine colorants.

Other ingredients which would act as colorants and modify the visual appearance of the post-foaming personal cleaning composition include opacifiers and pearlisers. Opacifiers may be selected from styrene/acrylate co-polymers, or waxes such as glyceryl stearate. Pearlisers may include glycol stearates such as ethylene glycol mono-stearate (EGMS), ethylene glycol di-stearate (EGDS), or inorganic particulates such as Mica.

Chelants include compounds which are capable of undertaking reversible binding (complexation) of a ligand (the chelant) to a metal ion and forming a metal complex (the chelate). Suitable chelants for use in the post-foaming personal cleaning composition include acetylacetone, aminoethylethanolamine, BAPTA, 2,2'-bipyridine, 1,2-bis(diphenylphosphino)ethane, citric acid, corrole, crown ether, 18-crown-6, cryptand, cyclen, DTPA, deferasirox, deferiprone, deferoxamine, dexrazoxane, diethylenetriamine, diglyme, dimercaprol, 2,3-dimercapto-1-propanesulfonic acid, dimercaptosuccinic acid, dimethylglyoxime, dithiolene, EDTA, EGTA (chemical), 1,2-ethanedithiol, ethylenediamine, gluconic acid, nitrilotriacetic acid, penicillamine, pentetic acid, phenanthroline, O-phenylenediamine, porphin, porphyrin, pyrocatechol, scorpionate ligand, sodium citrate, sodium diethyldithiocarbamate, sodium poly(aspartate), terpyridine, tetramethylethylenediamine, 1,4,7-triazacyclononane, 1,4,7-trithiacyclononane, or any combination thereof.

Vitamins which may be added to the post-foaming cleaning composition are those commonly known as vitamin nutrients essential for the human body. Suitable vitamins may be selected from vitamins A, $B_1$, $B_2$, $B_3$, $B_5$, $B_6$, $B_7$, $B_9$, $B_{12}$, C, D, E, K, or any combination thereof.

Skin conditioners, may include alkoxylated methyl glucose derivatives, for example, polypropylene glycol-20 methyl glucose ether, polypropylene glycol-10 methyl glucose ether, and polyethylene glycol ether of methyl glucose. Other skin conditioners that may be employed include allantoin, d- or dl-panthenol, sodium 2-pyrrolidone carboxylic acid and the like.

Moisturisers are compounds or mixtures of compounds which act to make the user's skin softer and more pliable by increasing its hydration. Suitable moisturisers include humectants, such as glycerin, urea, lactic acid and sorbitol; or natural moisturising factors including low molecular weight substances such as ammonia, aminoacids, glucosamine, creatinine, citrate and ionic solutions such as sodium, potassium, chloride, phosphate, calcium and magnesium.

Emollients, may also be used as skin conditioners, acting to reduce loss of water and as a softener of skin, by means of lubrication and smoothing. Suitable emollients include lanolin or cyclopentasiloxane. Alternatively, oil-water emulsions of varying compositions may be used, including several esters and oils such as octyl dodecanol, hexyl decanol, oleyl alcohol, decyl oleate, isopropyl stearate, isopropyl palmitate, isopropyl myristate, hexyl laureate, and dioctyl cyclohexane.

Many types of fragrances can be employed in the present invention, the only limitation being the compatibility with the other components being employed. Suitable fragrances include, but are not limited to, fruits such as almond, apple, cherry, grape, pear, pineapple, orange, strawberry, raspberry, musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

Preservatives may be present to retard spoilage of the composition. Suitable preservatives which may be used include phenoxyethanol, methyldibromo glutaronitrile, methyl paraben, ethyl paraben, propyl paraben, butyl paraben, isobutyl paraben, sodium benzoate, disodium EDTA, tetrasodium EDTA, DMDM hydantoin, methylchloroisothiazolinone, and methylisothiazolinone.

Humectants are hygroscopic substances often with several hydrophilic groups, most often hydroxyl groups, but may comprise amines and carboxyl groups, sometimes esterified, as well. Suitable humectants which may be used in the present invention include glycerine, propylene glycol (E 1520) and glyceryl triacetate (E1518); polyols such as sorbitol (E420), xylitol and maltitol (E965); polymeric polyols like polydextrose (E1200); natural extracts like quillaia (E999); lactic acid or urea.

pH modifiers include compounds which are suitable for adjusting and/or maintaining the pH of the post-foaming personal cleaning composition at a desired level. Suitable pH modifiers include alkali metal hydroxides such as sodium hydroxide, potassium hydroxide; alkali metal carbonates such as sodium carbonate, potassium carbonate; ammonia and alkyl amines such as diethylamine, triethyl amine; or citric acid, tartaric acid, phosphoric acid, hydrochloric acid, maleic acid, lactic acid, and sodium hydroxide.

Natural extracts suitable for use in the post-foaming personal cleaning composition may include agar oil, ajwain oil, angelica root oil, anise oil, balsam oil, basil oil, bergamot oil, black pepper, cannabis flower essential oil, caraway oil, cardamom seed oil, cedarwood oil, chamomile oil, cinnamon oil, cistus, clary sage, coriander, costmary oil (bible leaf oil), cranberry seed oil, cypress, davana oil, dill oil, fenugreek oil, fir, frankincense oil, galbanum, geranium oil, ginger oil, goldenrod, grapefruit oil, henna oil, helichrysum, hyssop, idaho tansy, jasmine oil, juniper berry oil, lavender oil, ledum, lemon oil, lemongrass, litsea cubeba oil, marjoram, melissa oil (lemon balm), mentha arvensis oil/mint oil, mountain savory, nutmeg, orange oil, oregano oil, orris oil, palo santo, parsley oil, patchouli oil, perilla essential oil, peppermint oil, petitgrain, pine oil, ravensara, red cedar, roman chamomile, rose oil, rosehip oil, rosemary oil, rosewood oil, sage oil, sandalwood oil, sassafras oil, savory oil, schisandra oil, spearmint oil, spikenard, spruce, star anise oil, tangerine, tarragon oil, tea tree oil, thyme oil, tsuga, valerian, vetiver oil (khus oil), western red cedar, wintergreen, yarrow oil, or ylangylang.

Minerals include chemical elements, other than carbon, hydrogen, nitrogen, and oxygen, which are required by humans, either in bulk amounts (RDA>200 mg/day), or trace amounts (<200 mg/day). Suitable bulk minerals include calcium, magnesium, phosphorus, potassium, sodium, or sulphur. Suitable trace minerals include chromium, cobalt, copper, fluorine, iodine, iron, manganese, molybdenum, selenium, or zinc. Other suitable minerals include bismuth, boron, nickel, rubidium, silicon, tellurium, titanium, tungsten, or vanadium.

It will be understood that the further other optional ingredients may be present in the post-foaming personal care composition in any amount suitable to provide the effect desired.

DESCRIPTION OF THE DRAWINGS

The invention is further illustrated by the following Examples, reference being also made to the accompanying drawings in which.

EXAMPLES

Example 1

The following base material was prepared (all percentages by weight based on the weight of the final composition)

| | |
|---|---|
| Cocamidopropyl betaine | 1.5% |
| Cocamidopropyl betaine & glyceryl Laurate Blend | 7.0% |
| Aminoxide | 0.9% |
| Sodium lauryl ether sulphate | 18.0% |
| Hydroxypropyl Triammonium Guar | 0.3% |
| Fragrance | 0.7% |
| Water (value adjusted to) | 71.6% |

The resultant base material had a viscosity of 127,500 cps using a Brookfield viscometer (spindle 4/speed/1). Isopentane was added in the amount of 10% and the resultant composition charged into a bag within an aerosol container.

Butane was used as the propellant gas outside the bag.

The composition was dispensed as a thick shear thinning gel. Foaming started after dispense and the foaming action was increased by agitation of the gel.

The invention is not limited to the above described specific embodiment and many variations and modifications can be made. In particular the invention is not restricted to shower gels and can be applied to other personal cleaning compositions such as hand wash and facial wash compositions and the like.

Figure 1:
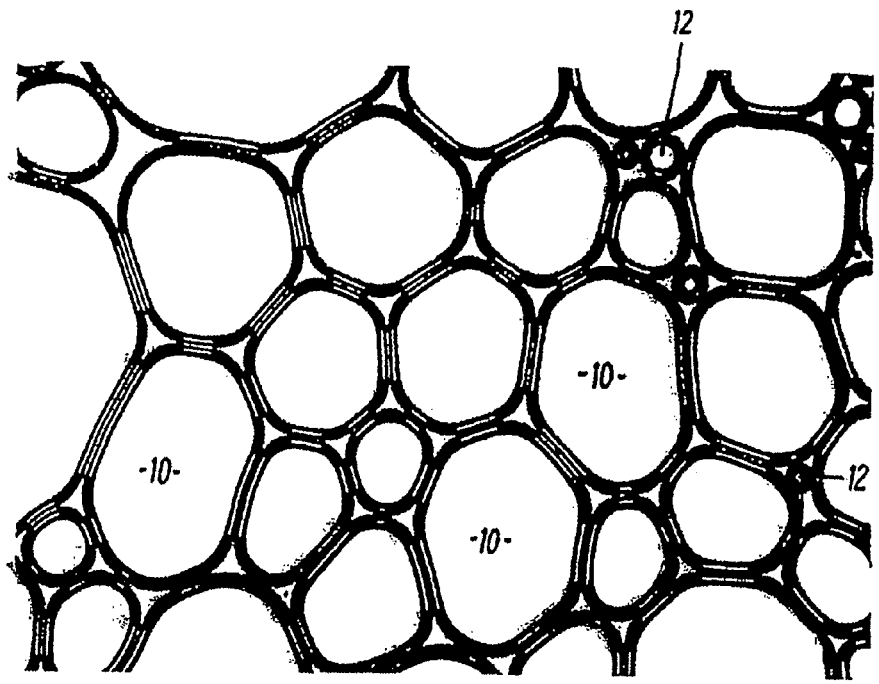
FIG. 1 shows the foam of the invention magnified ten times.
Figure 2:
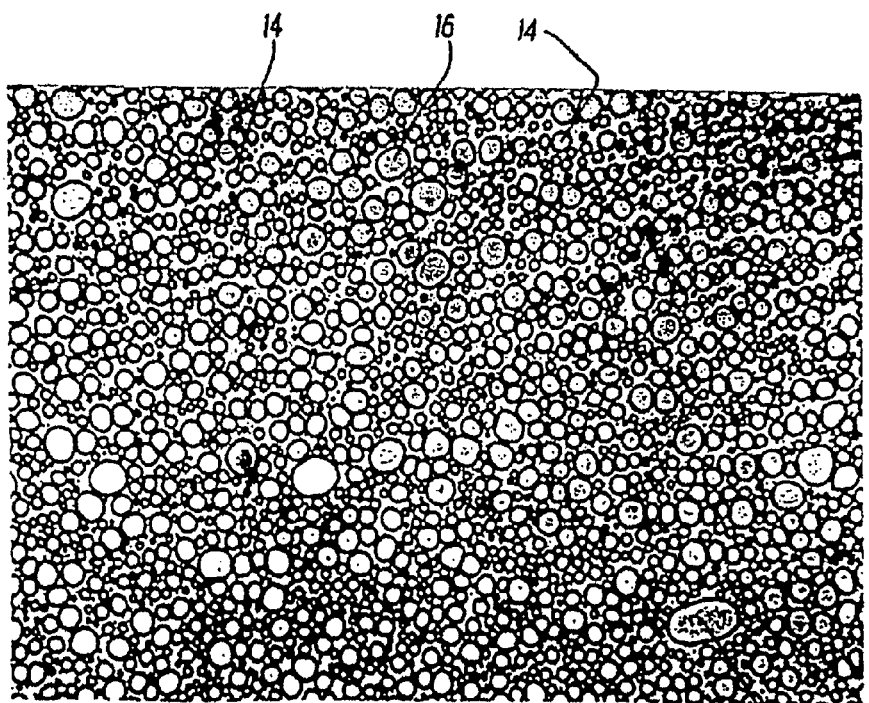
FIG. 2 shows a prior art shaving foam also magnified ten times.

The foam of the invention was examined under a microscope at ten times magnification and the result is shown in FIG. 1. As can be seen from the Fig. the foam consists of quite large cells 10 of varying shapes with smaller cells 12 filling in spaces between the larger cells. FIG. 2 shows the foam produced from a prior art post foaming gel intended for shaving. That foam consists of much smaller, substantially circular cross section cells 14 with a few somewhat larger cells 16 interspersed at random intervals amongst the smaller cells.

The large cell structure of the foam produced by the composition of the invention is believed to be, at least in part, due to the amount of propellant in the composition. Further when the composition is used in a hot shower, the effect of heat on the composition is to cause the propellant to boil off quickly so that a large amount of foam is produced.

The composition of the invention was submitted to a test panel to assess various attributes or properties thereof. The panel also assessed the same attributes of a conventional bath foam and a conventional tablet of soap. The procedure was as follows:

A small amount of each product was dispensed onto each panellists' hand except for the tablet of soap which was used directly. Each panellist "lathered" (i.e. agitated the product) for 15 seconds followed by rinsing for 15 seconds. They then dried their hands with a towel. They were asked to award a score in respect of various attributes in accordance with the following Table 1.

TABLE 1

| 1. Ease of Spreading | | | | |
|---|---|---|---|---|
| V Difficult | Difficult | Moderate | Easy | V Easy |
| 1    2 | 3    4 | 5    6 | 7    8 | 9    10 |

| 2. Rate of Lather Build Up | | | | |
|---|---|---|---|---|
| V Slow | Slow | Moderate | Fast | V Fast |
| 1    2 | 3    4 | 5    6 | 7    8 | 9    10 |

| 3. Amount of Lather | | | | |
|---|---|---|---|---|
| V Little | Little | Medium | Much | V Much |
| 1    2 | 3    4 | 5    6 | 7    8 | 9    10 |

| 4. Lather Texture | | | | |
|---|---|---|---|---|
| V Thin | Thin | Moderate | Creamy | V Creamy |
| 1    2    3 | 4    5 | 6    7 | 8    9 | 10 |

| 5. Ease of Rinsing | | | | |
|---|---|---|---|---|
| V Difficult | Difficult | Moderate | Easy | V Easy |
| 1    2 | 3    4 | 5    6 | 7    8 | 9    10 |

| 6. Feel of Wet Hands | | | | | | | | |
|---|---|---|---|---|---|---|---|---|
| Dislike Extremely | Dislike V Much | Dislike Moderately | Dislike Slightly | Neither like Nor Dislike | Like Slightly | Like Moderately | Like V Much | Like Extremely |
| 1 | 2 | 3 | 4 | 5 | 6 | 7 | 8 | 9 |

Dry Hands
7. Smoothness

| V Rough | Rough | Medium | Smooth | V Smooth |
|---|---|---|---|---|
| 1    2 | 3    4 | 5    6 | 7    8 | 9    10 |

| 8. Softness | | | | |
|---|---|---|---|---|
| V Harsh | Harsh | Medium | Soft | V Soft |
| 1    2 | 3    4 | 5    6 | 7    8 | 9    10 |

| 9. Overall Product Acceptance | | | | | | | | |
|---|---|---|---|---|---|---|---|---|
| Dislike Extremely | Dislike V Much | Dislike Moderately | Dislike Slightly | Neither like Nor Dislike | Like Slightly | Like Moderately | Like V Much | Like Extremely |
| 1 | 2 | 3 | 4 | 5 | 6 | 7 | 8 | 9 |

Skin Feel After 15 mins.
10. Smoothness

| V Rough | Rough | Medium | Smooth | V Smooth |
|---|---|---|---|---|
| 1    2 | 3    4 | 5    6 | 7    8 | 9    10 |

| 11. Softness | | | | |
|---|---|---|---|---|
| V Harsh | Harsh | Medium | Soft | V Soft |
| 1    2 | 3    4 | 5    6 | 7    8 | 9    10 |

| 12. Overall Product Acceptance | | | | | | | | |
|---|---|---|---|---|---|---|---|---|
| Dislike Extremely | Dislike V Much | Dislike Moderately | Dislike Slightly | Neither like Nor Dislike | Like Slightly | Like Moderately | Like V Much | Like Extremely |
| 1 | 2 | 3 | 4 | 5 | 6 | 7 | 8 | 9 |

The results of this evaluation are shown in Table 2.

TABLE 2

| Attribute | Bath Foam | Tablet Soap | Invention | Sig Level (Invention vs. Best Score) |
|---|---|---|---|---|
| Ease of Spreading | 6.2 | 7.05 | 7.85 | <0.1% |
| Rate of Lather Build Up | 5.2 | 6.15 | 9.1 | >0.1% |
| Amount of Lather | 5.05 | 5.7 | 9.1 | >0.1% |
| Lather Texture | 4.75 | 6.9 | 9.15 | >0.1% |
| Ease of Rinsing | 6.45 | 6.95 | 7.4 | >10% |
| Feel of Wet Hands | 5.4 | 5.45 | 6.65 | >0.1% |
| Smoothness | 6.5 | 6.0 | 7.25 | >1.0% |
| Softness | 6.55 | 5.95 | 7.65 | >0.1% |
| Overall Product Acceptance | 5.1 | 5.7 | 7.65 | >0.1% |
| Smoothness (after 15 mins) | 5.95 | 5.8 | 7.35 | >0.1% |
| Softness (after 15 mins) | 5.8 | 5.6 | 7.3 | >0.1% |
| Overall Product Acceptance (after 15 mins) | 5.1 | 5.25 | 7.3 | >0.1% |

The method of production of the composition of the invention using different materials is illustrated in the following Examples 2 to 5. The ingredients used in these Examples are listed in the following Table 3. For convenience the ingredients are referred to by the number in the table.

TABLE 3

| Ingredient (CTFA Name) | Trade Name | Supplier |
|---|---|---|
| 1). Sodium Lauryl Ether Sulphate SLES (25%) | — | Hickson-Manro |
| 2). Cocamidopropyl Betaine | (Tego Betain L7) | TH Goldschmidt AG. |
| 3). Aminoxide | (Aminoxide WS 35) | TH Goldschmidt AG. |
| 4). Disodium EDTA | — | — |
| 5). PEG 7 Glyceryl Cocoate | (Cetiol HE) | Henkel |
| 6). Hydroxypropyl Tri-ammonium Guar | (Jaguar C 162) | Rhone Poulenc |
| 7). Fragrance | — | — |
| 8). Coconut Diethanol amide | (Rewomid DC 212/S) | Rewo |
| 9). Sodium Cocoyl isethionate | (Elfan AT 84G) | Akzo-Nobel |
| 10). Sodium Cocoyl Glutamate | (Hostapon KCG) | Hoescht |
| 11). Preservative | (Euxyl K400) | Schulke & Mayr |
| 12). Cocoamidopropyl Betaine & Glyceryl Laurate | (Antil HS 60) | TH Goldschmidt AG. |
| 13). PEG 4 Rapeseed Amide | (Aminol N) | Chem-Y |
| 14). PEG 200 Glyceryl Hydrog. Palmiatate (and) PEG 7 Glyceryl Cocoate. | (Rewoderm L180) | Rewo |
| 15). Methyl Cellulose | (Benecel MP 943 W) | Aqualon |
| 16). Water | — | — |

The amounts of the ingredients used in the Examples is set out in the following Table 4.

TABLE 4

| | Example 2 | Example 3 | Example 4 | Example 5 |
|---|---|---|---|---|
| 1). | 71.50% | 54.0% | 71.50% | 71.50% |
| 2). | 5.00% | 5.00% | 5.00% | 5.00% |
| 3). | 1.00% | 1.00% | 1.00% | 1.00% |
| 4). | 0.15% | 0.1% | 0.15% | 0.15% |
| 5). | 1.0% | — | 1.0% | 1.0% |
| 6). | 0.3% | 0.5% | 0.3% | 0.3% |
| 7). | 0.7% | 0.7% | 0.7% | 0.7% |
| 8). | — | 1.0% | — | — |
| 9). | — | 5.0% | — | — |
| 10). | — | 3.36% | — | — |
| 11). | 0.08% | 0.08% | 0.08% | 0.08% |
| 12). | — | 8.00% | — | — |
| 13). | 5.00% | — | — | — |
| 14). | — | — | 5.00% | — |
| 15). | — | — | — | 1.0% |
| 16). | balance | balance | balance | balance |

Example 2

Water was added to (1). The betaine (2) was then added followed by (3). (4) was then dissolved in the mixture. (5) (6) and (7) were mixed together in a premix which was then added to materials (1)-(4). The preservative (11) was then added followed by (13) and the product mixed until a viscosity of 130,000 cps (Brookfield, Spindle RV 4, Speed 0.5) was built.

Example 3

(8) was dissolved in (16) and then added to (1), (2), (3) and (10) were then added along with (4) until dissolved (6), (7) and (8) were premixed and then added to the aforementioned ingredients. (11) was then added followed by (12) and the product mixed until a viscosity of above 100,000 cps (Brookfield, Spindle RV4, Speed 1) was built.

Example 4

Water was added to (1). The betaine (2) was then added followed by (3). (4) was then dissolved in the mixture. (5) (6) and (7) were mixed together in a premix which was then added to materials (1)-(4). The preservative (11) was then added followed by (14) and the product mixed until a viscosity of 60,000 cps (Brookfield, Spindle RV4, Speed 2) was built.

Example 5

Water was added to (1) followed by (15). The betaine (2) was then added followed by (3). (4) was then dissolved in the mixture. (5), (6) and (7) were mixed together in a premix which was then added to materials (1)-(4). The preservative (11) was then added. The viscosity was 26,800 cps (Brookfield, Spindle RV4, Speed 2)

The base materials prepared in the foregoing Examples 2 to 5 were mixed with isopentane (95%) in a 9:1 ratio to produce the post-foaming gel composition of the invention. The composition was then charged to an aerosol can in the same way as in Example 1.

What is claimed is:

1. A post-foaming personal cleaning composition in the form of a gel for use in an aerosol container, said composition consisting of:
   (a) a base material which consists of a surfactant in an amount not less than 7.0% by weight of the total composition and a thickener that is a blend of a glyceryl ester, with at least one of a betaine and a gum, said base material having a viscosity greater than 9,500 cps;

(b) a foam forming material, above 9% by weight of said composition, at least a part of the foam forming material being maintained in suspension in the composition until after the composition is dispensed from the aerosol, wherein the foam forming material is a saturated aliphatic hydrocarbon having from 4 to 5 carbons, and wherein the composition is in the form of a gel prior to inclusion of the foam forming material;

(c) water; and optionally, disodium EDTA, pH modifier, fragrance, preservative and colorant.

2. A composition as claimed in claim 1, wherein the viscosity is greater than 20,000 cps.

3. A composition as claimed in claim 1, wherein the viscosity is greater than 60.000 cps.

4. A composition as claimed in claim 1, wherein the glyceryl blend is present in an amount of from 5 to 10% by weight.

5. A composition as claimed in claim 1, wherein the surfactant is selected from the group consisting of anionic, cationic, nonionic, amphoteric surfactant, and mixtures thereof.

6. A composition as claimed in claim 1, wherein the surfactant is selected from a group consisting of one or more of alkyl polyglucosides, ethoxylated metal alkyl sulfonates, non-ethoxylated metal alkyl sulfonates, sultaines, taurates, sarcosinates, sulfonates, ether carboxylates, glycinates, quaternary ammonium compounds, polysorbates, sugar esters, alkyl phosphates, propionates, amino acid surfactants, glycosides, alkanolamides and betaines.

7. A post-forming personal cleaning composition for use in an aerosol container, said composition consisting of:

(a) a base material which consists of a surfactant in an amount not less than 7.0% by weight of the total composition and a thickener that is a blend of a glyceryl ester, with at least one of a betaine and a gum, said base material having a viscosity greater than 9,500 cps;

(b) a foam forming material, above 9% by weight of said composition, at least a part of the foam forming material being maintained in suspension in the composition until after the composition is dispensed from the aerosol, wherein the foam forming material is a saturated aliphatic hydrocarbon having from 4 to 5 carbons;

(c) water and optionally disodium EDTA, pH modifier, fragrance, preservative and colorant.

8. A composition as claimed in claim 7, wherein the viscosity is greater than 20,000 cps.

9. A composition as claimed in claim 7, wherein the viscosity is greater than 60,000 cps.

10. A composition as claimed in claim 7, wherein the glyceryl blend is present in an amount of from 5 to 10% by weight.

11. A composition as claimed in claim 7, wherein the surfactant is selected from the gourp consisting of anionic, cationic, nonionic, amphoteric surfactant, and mixtures thereof.

12. A composition as claimed in claim 7, wherein the surfactant is selected from a group consisting of one or more of alkyl polyglucosides, ethoxylated metal alkyl sulfonates, non-ethoxylated metal alkyl sulfonates, sultaines, taurates, sarcosinates, sulfonates, ether carboxylates, glycinates, quaternary ammonium compounds, polysorbates, sugar esters, alkyl phosphates, propionates, amino acid surfactants, glycosides, alkanolamides and betaines.

13. A composition as claimed in claim 7 wherein the composition is in the form of a gel prior to inclusion of the foam forming material.

* * * * *